(12) United States Patent
Listwan

(10) Patent No.: US 6,285,207 B1
(45) Date of Patent: Sep. 4, 2001

(54) METHOD AND APPARATUS FOR TESTING AN ELECTRICALLY CONDUCTIVE SUBSTRATE

(76) Inventor: Andrew Listwan, 3110 Woods Way, San Jose, CA (US) 95148

( * ) Notice: Subject to any disclaimer, the term of this patent is extended or adjusted under 35 U.S.C. 154(b) by 0 days.

(21) Appl. No.: 09/412,046

(22) Filed: Oct. 4, 1999

Related U.S. Application Data

(62) Division of application No. 08/698,509, filed on Aug. 15, 1996, now Pat. No. 5,999,012.

(51) Int. Cl.[7] .............................. G01R 31/28; G01R 31/00
(52) U.S. Cl. ............................................. 324/770; 324/753
(58) Field of Search ............................. 324/770, 96, 501, 324/537, 750, 753, 754

(56) References Cited

U.S. PATENT DOCUMENTS

| | | | |
|---|---|---|---|
| 3,934,199 | 1/1976 | Channin | 324/753 |
| 4,355,278 | 10/1982 | Burns et al. | 324/753 |
| 4,812,037 | 3/1989 | Riedel et al. | 324/501 |
| 4,820,976 | 4/1989 | Brown | 324/760 |
| 4,906,922 | 3/1990 | Takahashi et al. | 324/753 |
| 5,212,374 | 5/1993 | Speedy | 250/201.1 |
| 5,225,037 | 7/1993 | Elder et al. | 324/754 |
| 5,272,434 | 12/1993 | Meyrueix et al. | 324/753 |
| 5,311,137 | 5/1994 | Chang et al. | 324/501 |
| 5,412,866 | 5/1995 | Woith et al. | 324/754 |
| 5,504,438 | 4/1996 | Henley | 324/770 |
| 5,614,839 | * 3/1997 | Bosacchi | 324/770 |
| 5,734,158 | * 3/1998 | Nagashima et al. | 324/770 |
| 5,773,986 | 6/1998 | Thompson et al. | 324/754 |

* cited by examiner

Primary Examiner—Ernest Karlsen
(74) Attorney, Agent, or Firm—Fish & Richardson P.C.

(57) ABSTRACT

The method includes a step of contacting a surface of a sensing material to a surface of a substrate to form a mutual contact area between at least a portion of the surface of the sensing material and at least a portion of the surface of the substrate. The method also includes applying a first test signal to an electrode electrically connected to a component on the substrate. The method further includes illuminating the sensing material. The method also has a step of detecting light that has interacted with the sensing material to determine any changes induced in the sensing material by defects in the substrate manifest by applying the first test signal to the electrode. In an apparatus embodiment, a deformable sensing head is disclosed. The sensing head can be sensitive to voltage and heat changes on the substrate plate under test. In a preferred embodiment, the deformable sensing head has inflatable sensing material. The invention should have particular use in testing liquid crystal display panels.

7 Claims, 13 Drawing Sheets

METHOD AND APPARATUS FOR TESTING AN ELECTRICALLY CONDUCTIVE SUBSTRATE

This is a divisional of U.S. application Ser. No. 08/698,509, filed Aug. 15, 1996, now U.S. Pat. No. 5,999,012.

BACKGROUND OF THE INVENTION

The present invention relates generally to testing substrates and more particularly to testing electrically conductive substrates.

In recent years, small "laptop" computers have become popular. Because of their size and portability, small flat panel screens are used in laptop computers instead of more traditional video displays. FIG. 1A shows a laptop computer 10 with a flat panel display 12.

A side view of a typical flat panel display 12 is shown in FIG. 1B. During operation, selected pixels 14 on an active matrix plate are switched on or off. For a color display, the pixels 14 are grouped in triplets corresponding to the colors red, green, and blue. A liquid crystal 18 is sandwiched between the active matrix plate 16 and a color filter plate 20 having color filters 22. Seals 24 at edges of the flat panel display 10 uphold the active matrix plate 16, the liquid crystal 18, and the color filter plate 20 together and prevent the liquid crystal 18 from spilling out of the active matrix plate 16.

The pixels 14 which are turned on are set at various voltages. The voltages affect parallel and perpendicular dielectric constants of the liquid crystal 18. By changing these dielectric constants, the liquid crystal's ability to polarize light also changes. Light impinging upon the active matrix plate 16 is indicated by upward arrows in FIG. 1B. During operation, light shines through the active matrix plate 16 and is polarized in the liquid crystal 18. The light is then filtered by the color filters 22 to make an image on the flat panel display 12.

FIG. 1C shows a schematic representation of an active matrix 26 on an active matrix plate 16. Each pixel 14 is controlled by a transistor 28. By applying a voltage to one of an odd set of data electrodes 30 or even set of data electrodes 32, a source side of each transistor 28 can be biased. By applying another voltage to a gate of a selected biased transistor 28 via either odd gate electrodes 33 or even gate electrodes 34, a drain for the selected biased transistor 28 is activated, and a voltage is applied to the corresponding pixel 14. In this way, each pixel 14 in the active matrix plate 16 can be activated.

As with other electrical devices, flat panel displays 12 and the active matrix plates 16 are tested for quality assurance. FIG. 2A is a diagrammatic representation of a side view of a conventional active matrix plate tester 40. Under testing, a probe frame 42 with probe leads 43 sits atop the active matrix plate 16. The probe frame 42 electrically connects a pattern generator 44 to the data electrodes 30, 32 and gate electrodes 33, 34. The pattern generator 44 outputs voltages to the active matrix plate electrodes 30, 32, and 34 to activate the various transistors 28 and pixels 14.

Motors (not shown) horizontally and vertically position a sensing head 46 over a local area of the active matrix plate 16 to be tested. The plate rests on a support 45. Once positioned, other motors (not shown) orient the sensing head 46 with respect to an upper surface 48 of the active matrix plate 16. Similarly, a half-silvered mirror 50 is horizontally and vertically positioned and oriented with respect to the sensing head 46.

During testing, the pattern generator 44 attempts to activate a specific pixel or pixels 14 by sending voltages to the active matrix plate 16 as described above and electrically biasing a rigid sensing material 47 on the sensing head 46. The rigid sensing material 47 responds to voltage changes generated by the pixels 14 by changing its optical properties. The pattern generator 44 commands a light source 51 to shine a beam of light onto the half-silvered mirror 50. The half-silvered mirror 50 reflects the beam through the rigid sensing material 47 and sensing head 46. The light then travels down and is reflected back up by a mirrored bottom of the rigid sensing material 47. The reflected light then passes upward through the sensing head 46 and the half-silvered mirror 50.

A camera 52 photographs the reflected light. The pattern generator 44 directs the camera 52 to photograph the light once the sensing head 46 and the half-silvered mirror 50 are positioned and oriented and after the light source has emitted its beam of light.

Since the sensing head 46 can only be in proximity to part of the active matrix plate 16, the conventional active matrix plate tester 40 must make several iterations of the above procedure resulting in several pictures of local areas of the active matrix plate 16. Either before or after the camera 52 takes all the pictures, each picture is transferred into a digital format. Because the rigid sensing material 47 provides relatively weak optical signature, image processing is required to extract defect information from the digitized pictures. Therefore, an image processor 54 must process the pictures before defect patterns can be shown on a monitor 56.

FIG. 2B is a diagrammatic representation of a sensing head 46 while testing a local area of an active matrix plate 16. Generally, the rigid sensing material is glued to the sensing head 46. Because the sensing material 47 is rigid, the sensing material does not contact a surface 25 of the active matrix plate 16 because the rigid sensing material 47 may damage the active matrix plate 16. Furthermore, the surface irregularities create irregular distances between surface 25 of the active matrix plate 16 and the rigid sensing material 47. Thus, the sensitivity of the rigid sensing material 47 to pixel voltages is drastically degraded. Largely because of this, the pictures taken by the camera 52 must undergo image processing as described above.

FIG. 3 is a flow diagram summarizing a typical conventional method 60 of testing an active matrix plate 16 beginning at a step 62. This conventional method 60 was just described with reference to the conventional active matrix plate tester 40 in FIG. 2A. Initially, the active matrix plate 16 is placed in the tester 40 in a step 64. Then, the probe frame 42 is positioned on the active matrix plate 16 in a step 66. The sensing head 46 with the rigid sensing material 47 is then placed over a local area to be tested in a step 68 and the sensing head 46 and rigid sensing material 47 are oriented with respect to the local area in a step 70. In a step 72, the pattern generator 44 applies voltages to the active matrix plate 16 via data electrodes 30, 32 and gate electrodes 33, 34. Step 74 applies a voltage to bias the rigid sensing material 47 at an operating voltage. As with the light source 52 and half-silvered mirror 50 as discussed above, the local area is illuminated in a step 76. After being reflected off a bottom of the rigid sensing material 47 and passing through the rigid sensing material 47, the camera detects the light in step 78. The camera pictures are image processed in step 80 to remove noise.

Step 82 determines whether all test patterns for a particular voltage have been sent to the active matrix plate 16.

Generally, a voltage signal is applied to the odd electrodes 30 followed by the same signal to the odd electrodes 30 with negative voltage magnitude. Step 82 determines that not all signals have been applied after the positive and negative voltage signals have both been applied to the odd electrodes 30. Then the same signals are "reversed" in a step 84 by applying them to even electrodes 32. Steps 76, 78, and 80 are then repeated for the positive and negative voltage signals applied to the even electrodes 32. Then step 82 answers yes, and step 86 determines whether all local areas have been tested. If not, conventional method 60 returns to step 68 to repeat steps 68, 70, 72, 74, 76, 78, 80, 82, and 84 for a new local area. Once all local areas have been tested, step 86 passes to step 88 where an image indicating defects in the active matrix plate 16 is displayed. Conventional method 60 ends at step 90.

The conventional method 60 has several drawbacks. First, only a relatively small part of the matrix plate 16, or other substrate, can be tested at one time. For this reason, complex and cumbersome systems of motors are required to position and to orient the sensing head 46, the half-silvered mirror 50, the camera 52, or a support on which the plate 16 or substrate rests. Also, multiple steps are required to position and to orient the equipment over each local area.

Additionally, the gap between the sensing head material 47 and the top surface of the active matrix plate varies. Consequently, the amount of noise varies from local area to local area. It also varies within each local area as the gap between the rigid sensing material 47 and top surface 25 of the matrix plate 16 varies.

SUMMARY OF THE INVENTION

The present invention is directed to a method of testing an electrically conductive substrate. The method includes a step of contacting a surface of a sensing material to a surface of a substrate to form a mutual contact area between at least a portion of the surface of the sensing material and at least a portion of the surface of the substrate. The method also includes applying a first test signal to an electrode on the substrate. The method further includes illuminating the sensing material. The method also has a step of detecting light that has interacted with the sensing material to determine any changes induced in the sensing material by defects in the substrate manifest by applying the first test signal to the electrode.

In an apparatus aspect of the invention, a tester for detecting defects in the electrically conductive substrate is also disclosed. The tester includes a deformable sensing head having a sensing material sensitive to states of a substrate. The deformable sensing head is positioned such that the sensing material is in contact with, and conforms with, a portion of a surface of the substrate. The tester has a pattern generator electrically connected to an electrode electrically connected to a component on the substrate. The pattern generator produces an electrical test signal to activate the component via the electrode such that any defects in the electrode and the component are manifest as a state change of the substrate when the test signal is applied.

The present invention also includes an integrated probe frame for use in an electrically conductive substrate tester. The integrated probe frame includes a deformable sensing head having a sensing material sensitive to changes in state of a substrate under test. During testing the deformable sensing head is positioned such that the sensing material is in contact with a surface of the substrate. The sensing material also conforms with a portion of the surface of the substrate. The integrated probe frame also includes a probe lead engaged with the deformable sensing head and electrically connected to an electrode on the substrate under test. An alignment of the probe lead to the electrode requires at least a partial alignment of the deformable sensing head to the substrate under test.

Unlike conventional sensing heads and sensing materials, the deformable sensing head of the present invention permits the testing of an entire substrate all at once instead of only local areas. Therefore, the present invention results in large time savings. A typical substrate can be tested in roughly ten seconds with the present invention compared with over a minute using conventional methods. Such a time savings is greatly magnified when testing large numbers of substrates.

Additionally, the deformable sensing head conforms with the surface of the substrate thus obviating the gap problem inherent in conventional methods. Eliminating the gaps results in much higher resolution with much less image noise or blur. Consequently, electronic image processing is not required, and defects can be seen with the naked eye. When a camera is used and its pictures are digitized into raw electrical signals, the raw electrical signals can be displayed directly on a video monitor without image processing.

Unlike conventional methods, the tester can detect defects generating temperature changes on the substrate. In this embodiment, the sensing head has a heat sensitive sensing material.

The hardware setup is much simpler and costs much less for testing equipment of the present invention compared with conventional testing equipment. For example, complex mirror arrangements are unnecessary and fewer motors are required to position the deformable sensing head.

DETAILED DESCRIPTION OF PREFERRED EMBODIMENTS

Although the following will discuss the use of the invention to test active matrix plates, those skilled in the art will appreciate that other substrates can be tested with the present invention. For example, a semiconductor chip, a wafer, or other type of liquid crystal display panel besides an active matrix plate may be tested.

Figure 4A:
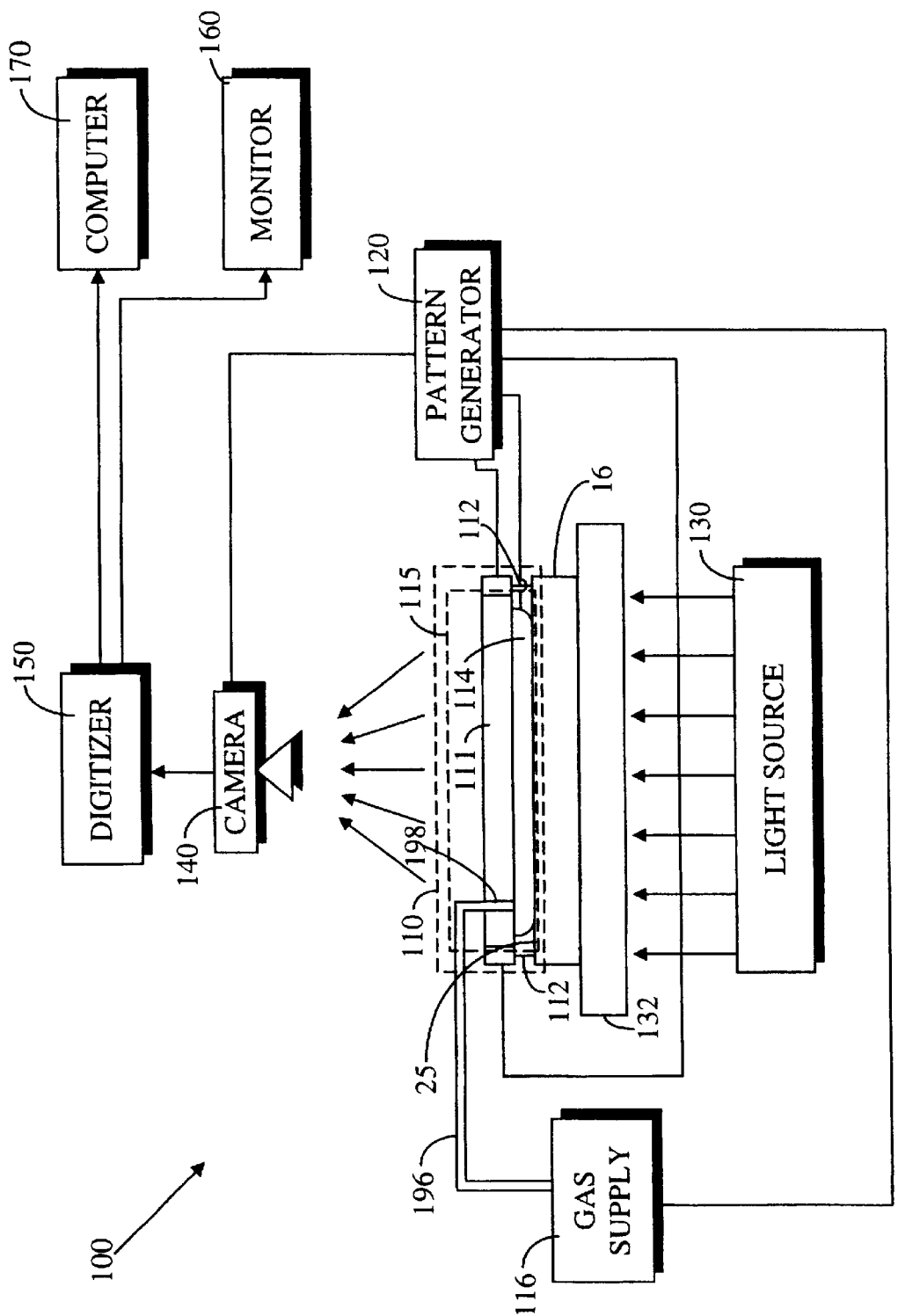
FIG. 4A is a diagrammatic representation of an embodiment of a tester for detecting defects in a substrate in accordance with the present invention.

FIG. 4A is a diagrammatic representation of a preferred embodiment of a tester 100 for detecting defects in an active matrix plate 16 in accordance with the present invention. The tester 100 has an integrated probe frame 110 with probe leads 112 electrically connected to odd electrodes 30, even electrodes 32, and data electrodes 34 on the active matrix plate 16 under test. The integrated probe frame 110 has sensing material 114 in contact with a top surface 25 of the active matrix plate 16. A transparent structure 111 attaches the sensing material 114 to the probe leads 112. As illustrated, a deformable sensing head 115 includes the transparent structure 111 and the sensing material 114. Suitable transparent structure materials include glass and plexiglass.

In other embodiments of the tester 100, the deformable sensing head 115 may be synonymous with the sensing material 114. For example, the integrated probe frame 110 may be replaced by a conventional probe frame and sensing material 114 without the transparent structure 111 to bind the sensing material 114 to the probe leads 112. Then the sensing material 114 should have a cavity if a fluid system such as a gas supply 116 is still used. Whether or not the fluid system is still used, the sensing material 114 in effect becomes the deformable sensing head 115. Of course, the sensing material 114 backed by the transparent structure Ill unattached to the probe leads 112 forms another embodiment of the deformable sensing head 115. This embodiment can also be used with a separate conventional probe frame.

The electrodes 30, 32, 33, and 34 are connected to components, such as transistors 28 and pixels 14, on the active matrix plate 16. As used herein, the electrodes 30, 32, 33 and 34 are construed to mean not only exposed conductors on the active matrix plate 16 but also electrical connections within the active matrix plate 16 which are capable of electrically connecting the components with external signals.

Figure 1A:
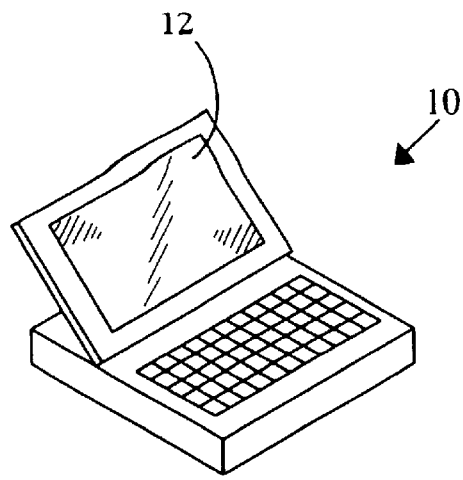
FIG. 1A is a diagrammatic representation of a laptop computer having a flat panel display.
Figure 1B:
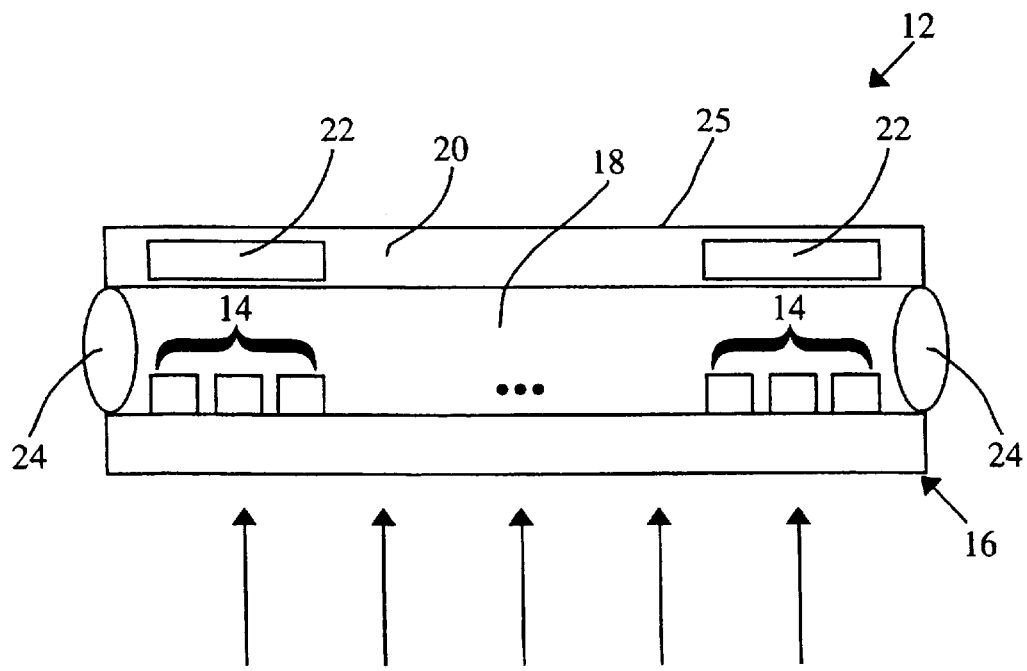
FIG. 1B is a diagrammatic representation of a side view of a flat panel display.
Figure 1C:
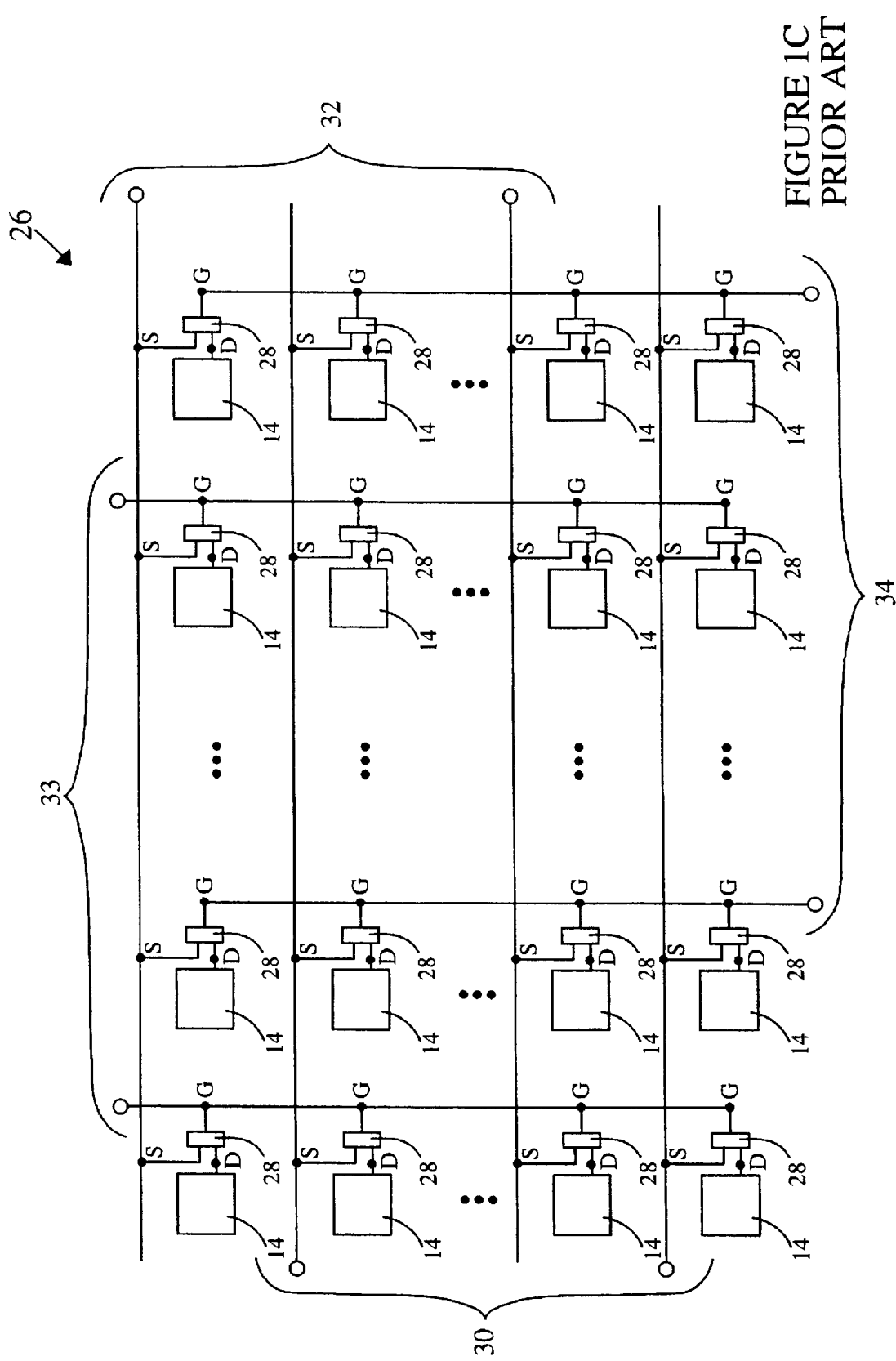
FIG. 1C is a schematic diagram of an active matrix.
Figure 2A:
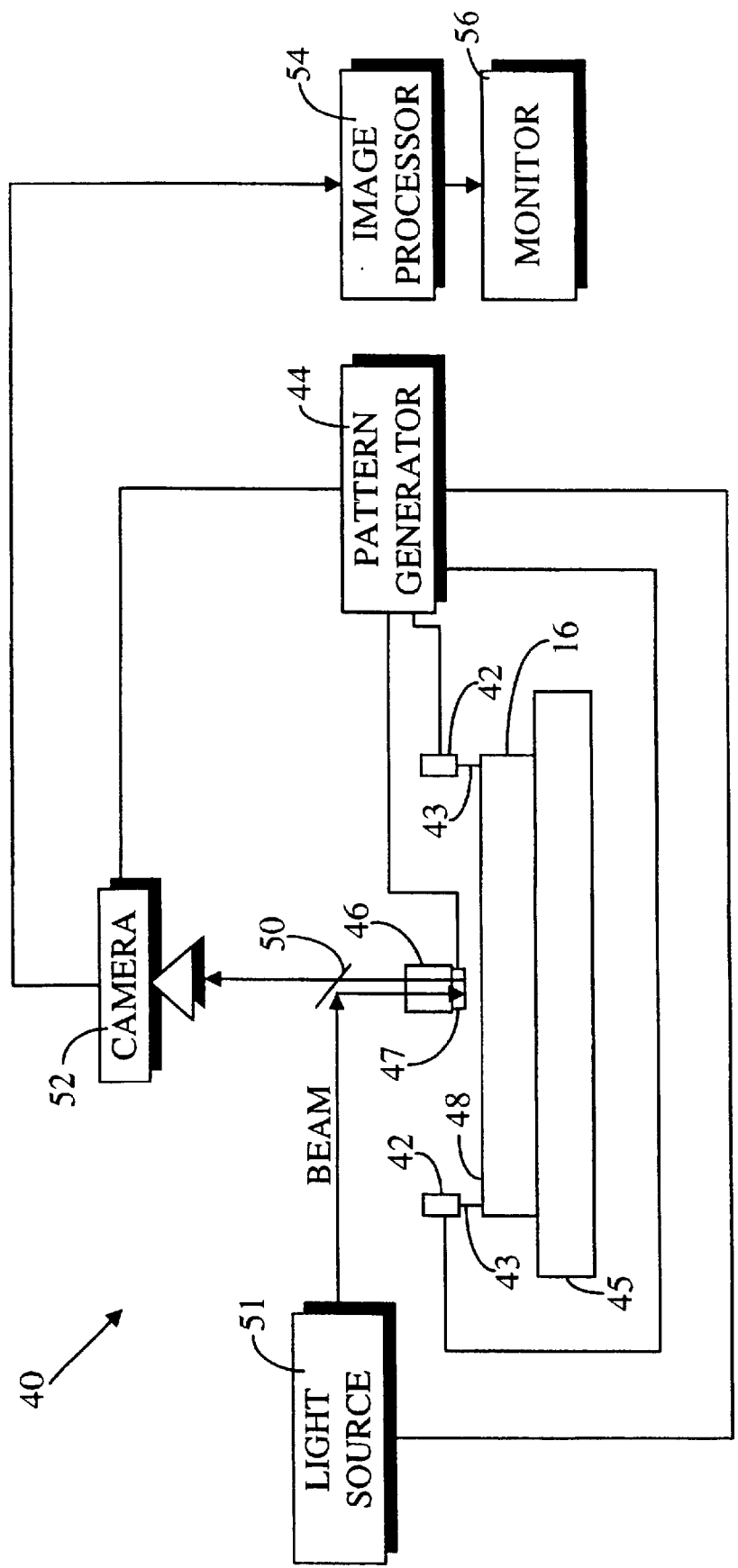
FIG. 2A is a diagrammatic representation of a conventional apparatus for testing a substrate.
Figure 2B:
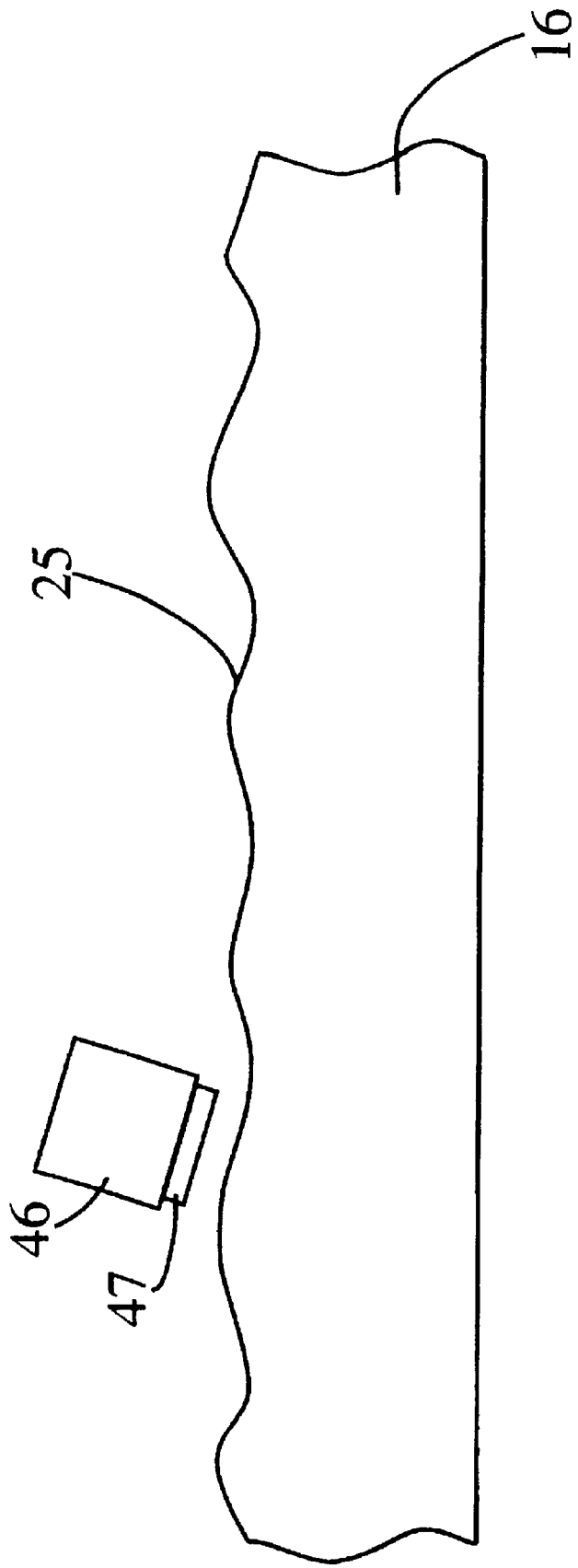
FIG. 2B is a diagrammatic representation of a conventional sensing head testing a local area of a substrate.
Figure 3:
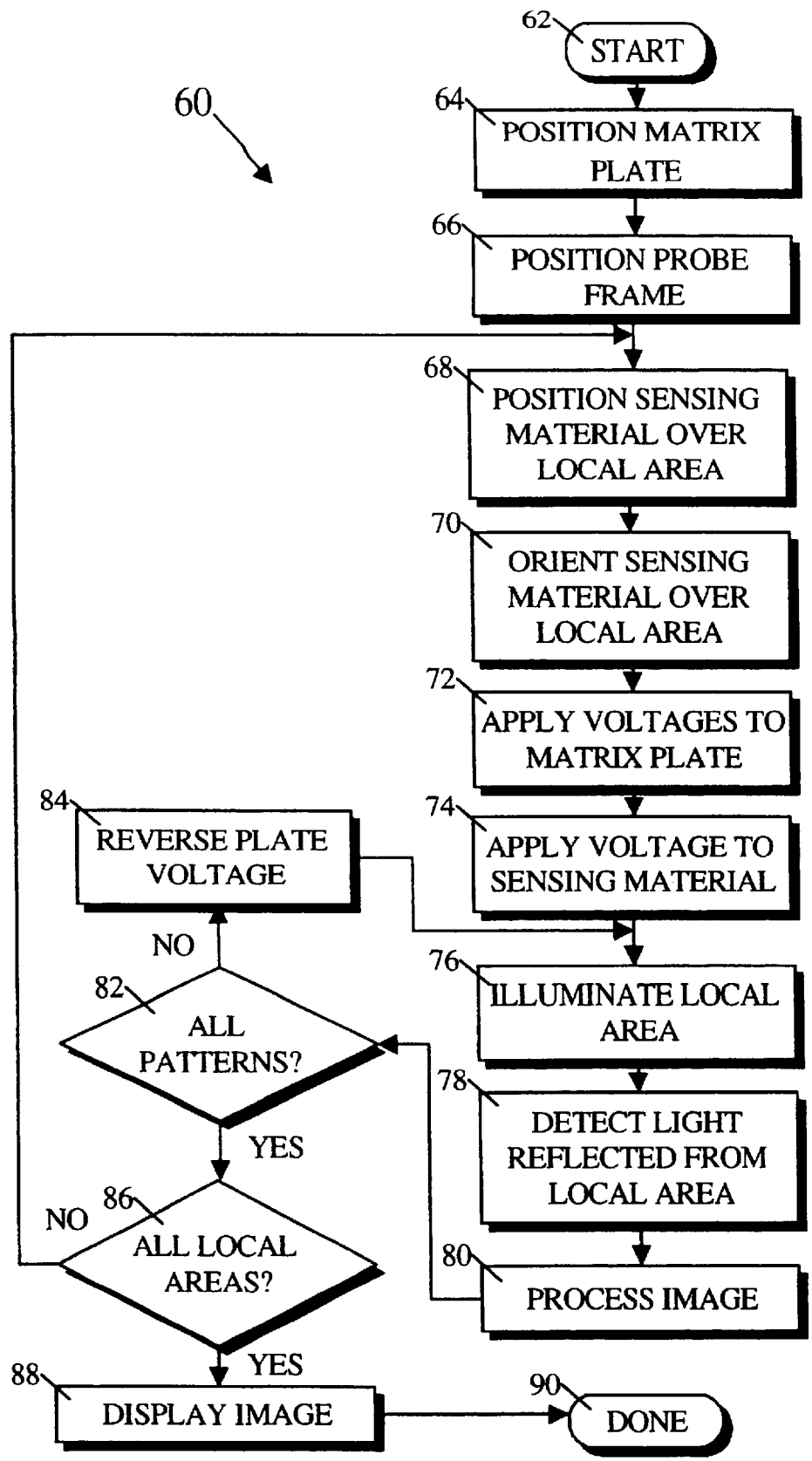
FIG. 3 is a flow diagram illustrating a conventional method of testing a substrate

During testing, the sensing material 114 is in contact with, and conforms with, a surface of the active matrix plate 16. Thus problems with surface irregularities of conventional sensing heads 46 and conventional rigid sensing materials 47 as illustrated in FIG. 2B are obviated. Because of this, and because the sensing head can have a relatively large mutual contact area 250 (see FIG. 8) obviating matching images for several local areas, the deformable sensing head 114 dramatically enhances testing resolution compared with conventional heads 46 and materials 47. Indeed, the present invention permits viewing of defects with the naked eye instead of via a camera, if desired.

In preferred embodiments, the sensing material 114 is sensitive to voltages or temperatures, or both, on the active matrix plate 16. Suitable voltage sensitive materials include polymer dispensed liquid crystals (PDLC). Conventional testers 40 are insensitive to heat changes on the plate 16 because of the rigid sensing material 47 is insensitive to the heat changes and has gaps between its bottom and the plate 16. Suitable heat sensitive materials include heat sensitive crystals.

In another preferred embodiment, the deformable sensing head 115 is compressible. In this case, the head can have clear silicone rubber covered with a voltage sensitive or heat sensitive sensing material 114. In another preferred embodiment, the deformable sensing head 115 is inflatable via a fluid system. For example, in FIG. 4A, a gas supply 116 inflates the sensing material via conduit 198 in the transparent structure 111.

A pattern generator 120 is electrically connected to the electrodes 30, 32, 33, and 34. Preferably, the pattern generator 120 makes these connections via the leads probe 112 on the integrated probe frame 110. The pattern generator 120 produces electrical test signals to activate components on the active matrix plate 16. In doing so, defects in the active matrix plate 16 are manifest as state changes in the active matrix plate 16. Such a state change may include temperature changes and voltage changes distributed on the active matrix plate 16.

The pattern generator 120 may send a biasing signal to bias the sensing material 114 at an operating voltage. This may be particular useful when the sensing material 114 is sensitive to voltages on the active matrix plate 16. However, in some embodiments the sensing material 114 is sensitive to voltage changes on the active matrix plate 16 without the biasing. Then the biasing signal would increase the sensing material's sensitivity to voltage changes. On the other hand, the sensing material 114 may require the biasing signal to be sensitive to the voltage changes. In either case, the biasing signal sensitizes the sensing material 114 to the defects manifest by the application of test signals by the pattern generator 120 to the active matrix plate 16.

A light source 130 illuminates the active matrix plate 16 and sensing material 114. A suitable light source 130 is a simple florescent lamp. In the preferred embodiment diagramed in FIG. 4A, the light source 130 is positioned beneath the active matrix plate 16. In this case, the active matrix plate 16 rests on a transparent support 132, and light from the light source 130 passes through the transparent support 132 and illuminates the active matrix plate 16. The transparent support is preferably quartz glass or plexiglass although other suitable materials may be used.

In a preferred embodiment, the sensing material 114 has an optical property which detectable when illuminated. When the sensing material 114 is voltage sensitive, the optical property varies over the sensing material 114 in response to a voltage distribution over the? matrix plate 16. Similarly, a second optical property varies over the sensing material 1 in response to a heat distribution over the active matrix plate when the sensing material 114 sensitive. Both optical properties permit the detection of defects. In some embodiments, the same optical property will depend upon both voltage and temperature. Optical properties of the sensing material 114 include color, ability to polarize light, transmissibility, color density, darkness, contrast, hue, and tint.

Although the effects of the optical properties of the sensing material 114 on the light can be viewed or "detected" with the naked eye, it may be convenient to detect the light with a camera 140. The camera may take still or moving pictures. Preferably, the camera has a high enough resolution and wide enough angle lens that only one picture for a given test pattern transmitted to the active matrix plate 16 is required.

In preferred embodiments, the camera pictures are digitized into raw electrical signals by a digitizer 150 containing an analog to digital converter. The digitizer 150 may be included in the camera 140. Because of the dramatically improved picture resolution over conventional methods due to the sensing material 114 having the mutual contact area 250 with the top surface 25, image processing of the pictures is unnecessary. Therefore, the raw electrical signals can be displayed directly on a video monitor 160 without modification. Optionally, an image processor (not shown) may process the raw electrical signals output by the digitizer 150.

Additionally, the digitized pictures may be sent to a computer 170 for tab f defects. The computer 170 information may store defect image data in any of a variety of media and devices including a hard disk, floppy disk, RAM, compact disk, and tape. The computer runs algorithms to store and tabulate the image data. The computer 170 need not be used in tandem with the monitor 160. Similarly, the tester 100 may only have the monitor 160 and not the computer 170. The computer 170 and monitor 160 provide ways of accessing the results of testing.

Many of the above mentioned devices may be combined in other embodiments. For example, combinations of the pattern generator 120, the digitizer 150, the monitor 160, and the computer 170 may be included in one submachine included in the tester 100. Similarly, the digitizer 150 may be part of the camera 140, and the monitor 160 may be part of the computer 170.

Figure 4B:
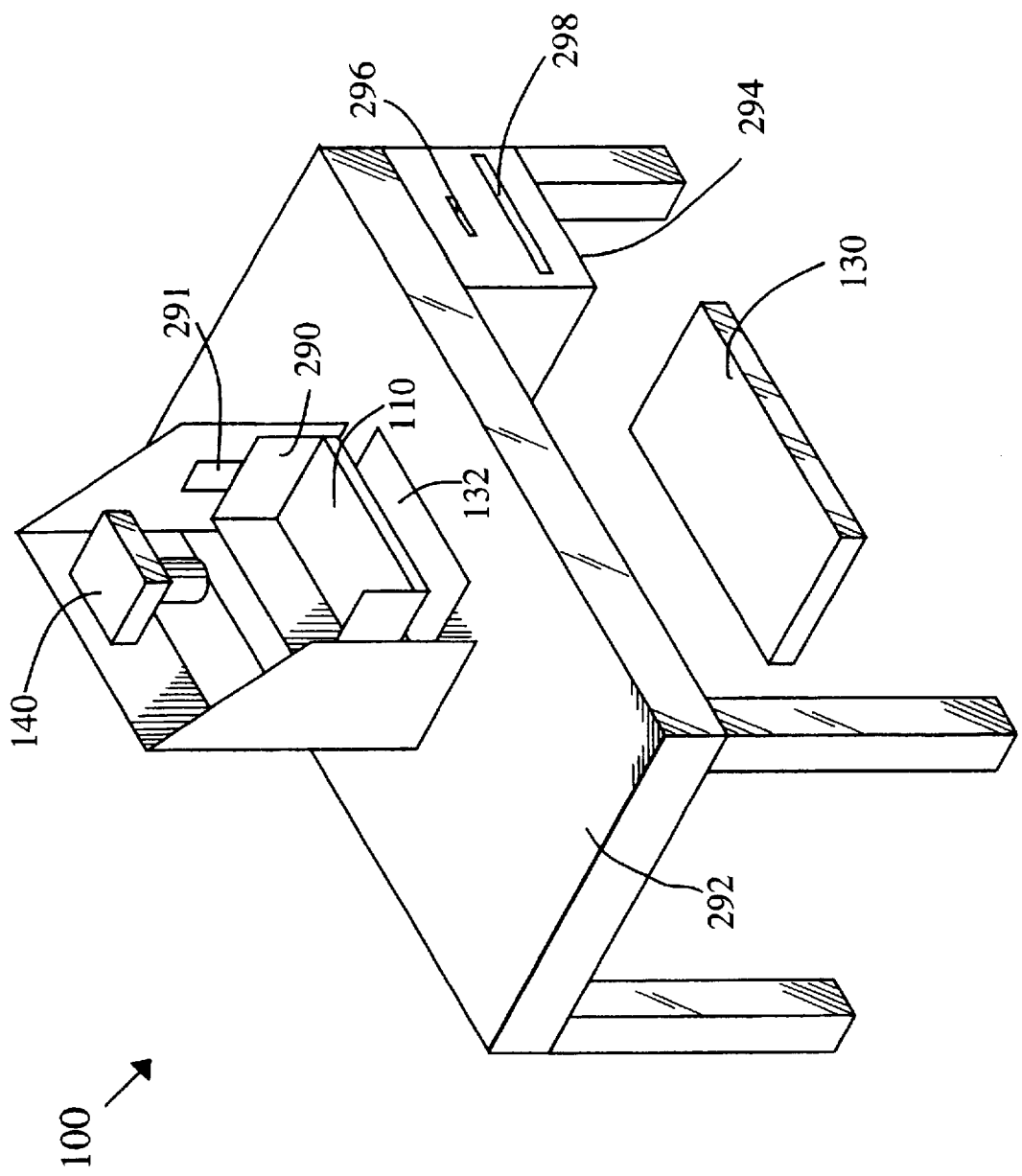
FIG. 4B is a diagrammatic representation of an embodiment of a tester for detecting defects in a substrate in accordance with the present invention.

FIG. 4B is a sketch of a preferred embodiment of the tester 100. As shown, the integrated probe frame 110 is contained in a holder 290 above the transparent support 132. The holder 290 is slidably connected to a post 291. Presently, a gas pump is preferred to move the holder 290 up and down. During operation, the holder 290 moves up and down along the post 291 as plates 16 are tested. The holder 290 and integrated probe frame to contact the integrated probe frame 110 and sensing material 114 to the active matrix plate 16 under test.

The transparent support 132 is a glass window in a table 292. The flourescent light source 130 is beneath the table 292. Light from the flourescent light source 130 shines up through the transparent support 132 and illuminates the active matrix plate 16. The camera 140 is supported above the integrated probe frame 110. Light shining through active matrix plate 16 is photographed by the camera 140 suspended above the holder 290 when the holder 290 and integrated probe frame 110 are in the down position. The pattern generator 120 and computer 170 are housed in a metal container 294 underneath the table 292 in this embodiment. The computer 170 can write the data to a floppy disk in a floppy drive 296 or to a compact disk in a compact disk drive 298. As noted above, the computer 170 may write to other storage devices.

Figure 4C:
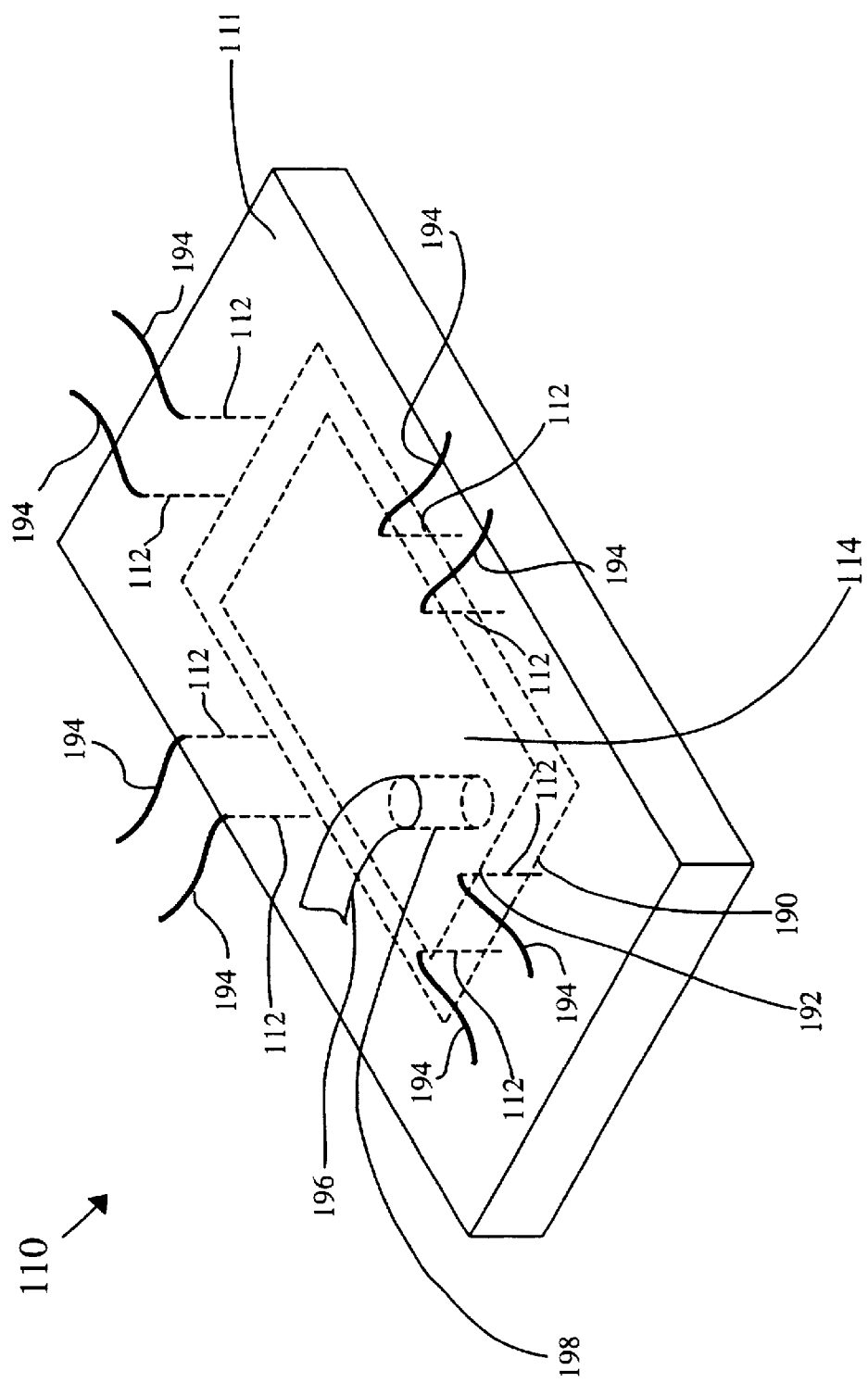
FIG. 4C is a diagrammatic representation of an embodiment of a probe frame and deformable sensing head in accordance with the present invention.

FIG. 4C is sketch of an embodiment of the integrated probe frame 110 of the present invention. Dashed lines show a boundary 190 of the sensing material 114 attached underneath a transparent structure 111. The sensing material 114 is glued onto the transparent structure 111. Glue is applied between boundary 190 and glue line 192. Probe leads 112 go through a top surface of the transparent structure 111 and have exposed contacts jutting from the bottom of the transparent structure 111. Wires 194 connect the probe leads 112 to the pattern generator 120 (not shown). The exposed contacts make electrical contact with the data electrodes 30, 32, and the gate electrodes 33, 34. As noted on FIG. 4A and the accompanying discussion, the integrated probe frame 110 includes a deformable sensing head 115 having the transparent structure 11 and the sensing material 114. A deformable sensing head 115 separate from the integrated probe frame 110 could be made by simply by removing the probe leads 112.

A tube 196 connects the gas supply 116 (not shown) to a conduit 198 between the top and bottom surfaces of the transparent structure 111. As the gas supply pumps gas through the conduit 198, a space formed by the glue, the sensing material 114, and the bottom surface of the transparent structure 111 fills with gas. Consequently, the sensing material 114 becomes inflated.

Figure 5:
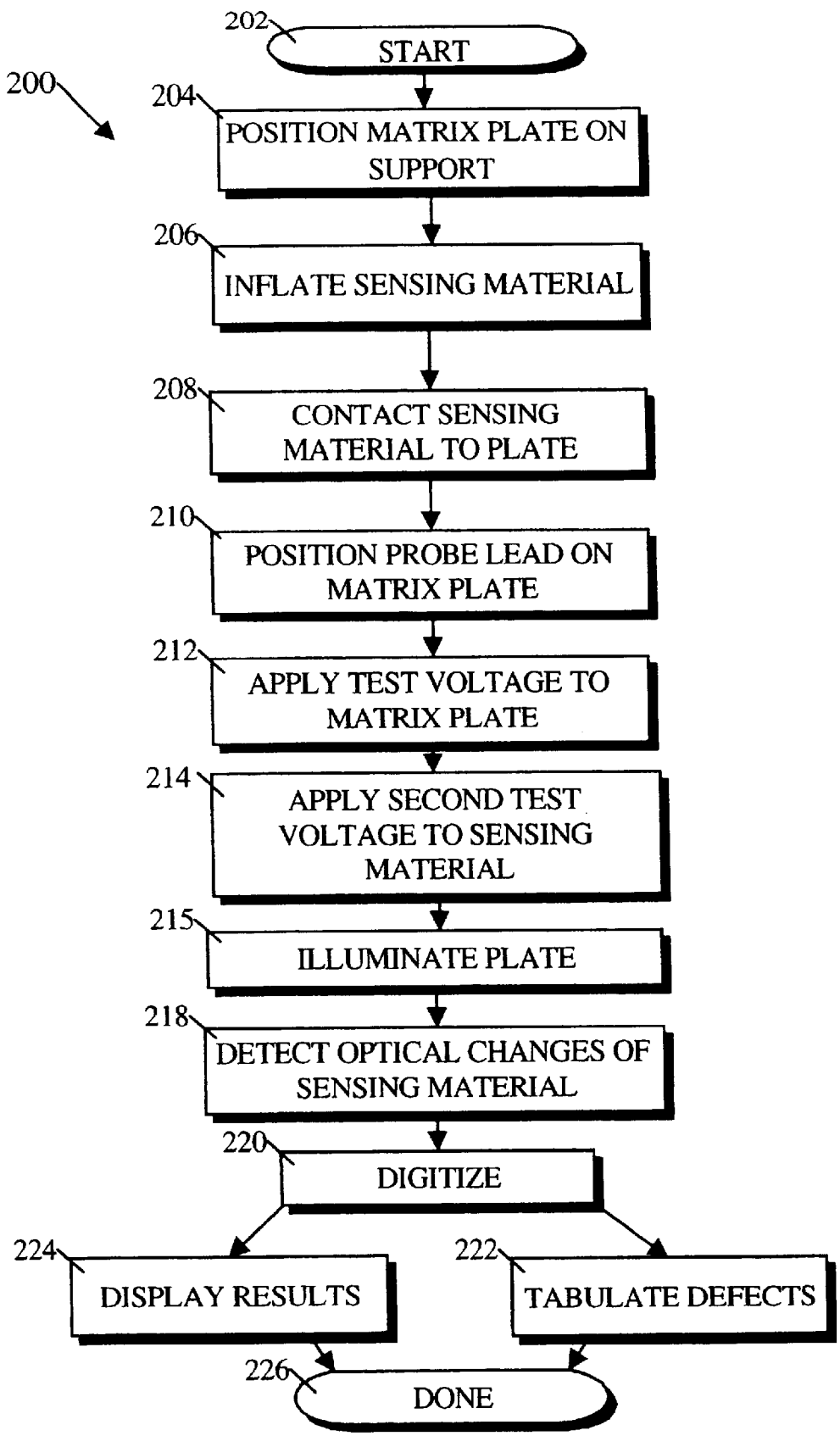
FIG. 5 is a flow diagram illustrating an embodiment of the present invention of testing a substrate.

An overview of a preferred method 200 of testing an active matrix plate 16 used in a video display is shown in a flow diagram in FIG. 5 beginning at a step 202. Step 204 places the active matrix plate 16 on a the transparent support 132. Step 204 may include a substep of aligning the plate with specific points on the transparent support 132. In some embodiments, robotic arms or levers may set the active matrix plate 16 on the transparent 2 and align the plate 16.

The sensing material is then inflated in a step 206. As noted above, the sensing material 114 may be inflated by a fluid system such as a gas supply 116. The deformable sensing head 115 with sensing material 114 are then lowered in a step 208 to contact the active matrix plate to form a mutual contact area 250 between a portion of a surface of the sensing material and a portion of a surface of the active matrix plate 16 as diagrammed in FIG. 8. In a preferred embodiment, the sensing material 114 is inflated to have a convex surface. The convexity causes the mutual contact area to increase as the deformable sensing head 115 is lowered. This effect of convex sensing material 114 minimizes air bubbles which might form as the sensing material contacts the top surface 25 of the active matrix plate 16.

In other embodiments, the sensing material 114 will not be inflated. For example, the deformable sensing head 115 may be compressible with the sensing material 114 covering a compressible substance such as clear silicone rubber. Alternatively, the deformable sensing head may not have the compressible substance and the sensing material 114 itself would be compressible. In either case, preferred embodiments make the sensing material 114 assume a convex shape before contacting the surface 25 of the active matrix plate 16. Then a convex compressible sensing material 114 minimizes potential air bubbles in the same way as the convex inflatable sensing material 114.

Step 210 positions a probe lead 112 of the integrated probe frame 110 on a matrix plate electrode. For the tester 100 illustrated in FIG. 4B, step 210 coincides with lowering the holder 290 along the post 291. If an integrated probe frame 110 is being used, steps 208 and 210 may occur simultaneously if the inflated sensing material 114 extends the same distance below the transparent substrate 111 as the probe lead(s) 112. If the inflated sensing material 114 extends farther below the probe lead(s) 112, step 208 occurs before step 210. Then, the mutual contact area 250 increases as step 210 positions the probe lead 112. If the deformable sensing head 115 can move independently of the probe leads, step 210 will be distinct from step 208.

Clearly, steps 206, 208, and 210 may be permuted to form a different embodiment of the present invention method 200.

For example, the sensing material 114 may contact the matrix plate 16 before it is inflated in step 206. Also, the probe lead may be positioned in step 210 before the sensing material 114 is inflated in step 206 and before the sensing material contacts the matrix plate surface in step 208 when the probe leads extend farther below than the sensing material 114.

The pattern generator 120 or other signaling equipment applies a test voltage to the electrodes on the active matrix plate in step 212. This test voltage can simply be a pulse or a more complex signal or pattern. The test voltage activates components, such as transistors 28 and pixels 14, via electrodes 30, 32, 33, and 34 and lead traces interconnecting components on the active matrix plate 16. In step 214, the pattern generator 120 sends a second test signal to the sensing material 114 to bias it at an operating point and thus sensitize the material 114 to defects in the plate 16.

After the voltages are applied, the matrix plate is illuminated in step 216 by a light source 130. As described above with reference to FIGS. 4A and 4B, the light interacts with the sensing material 114 and is detected. Preferably, a camera 140 detects the light. Changes in the optical properties of the sensing material 114 manifest by the application of the first test voltage to the plate show defects in the plate 16. Thereafter, the pictures are digitized in step 220. Defects are tabulated in step 222, and the pictures are displayed in step 224.

Figure 6:
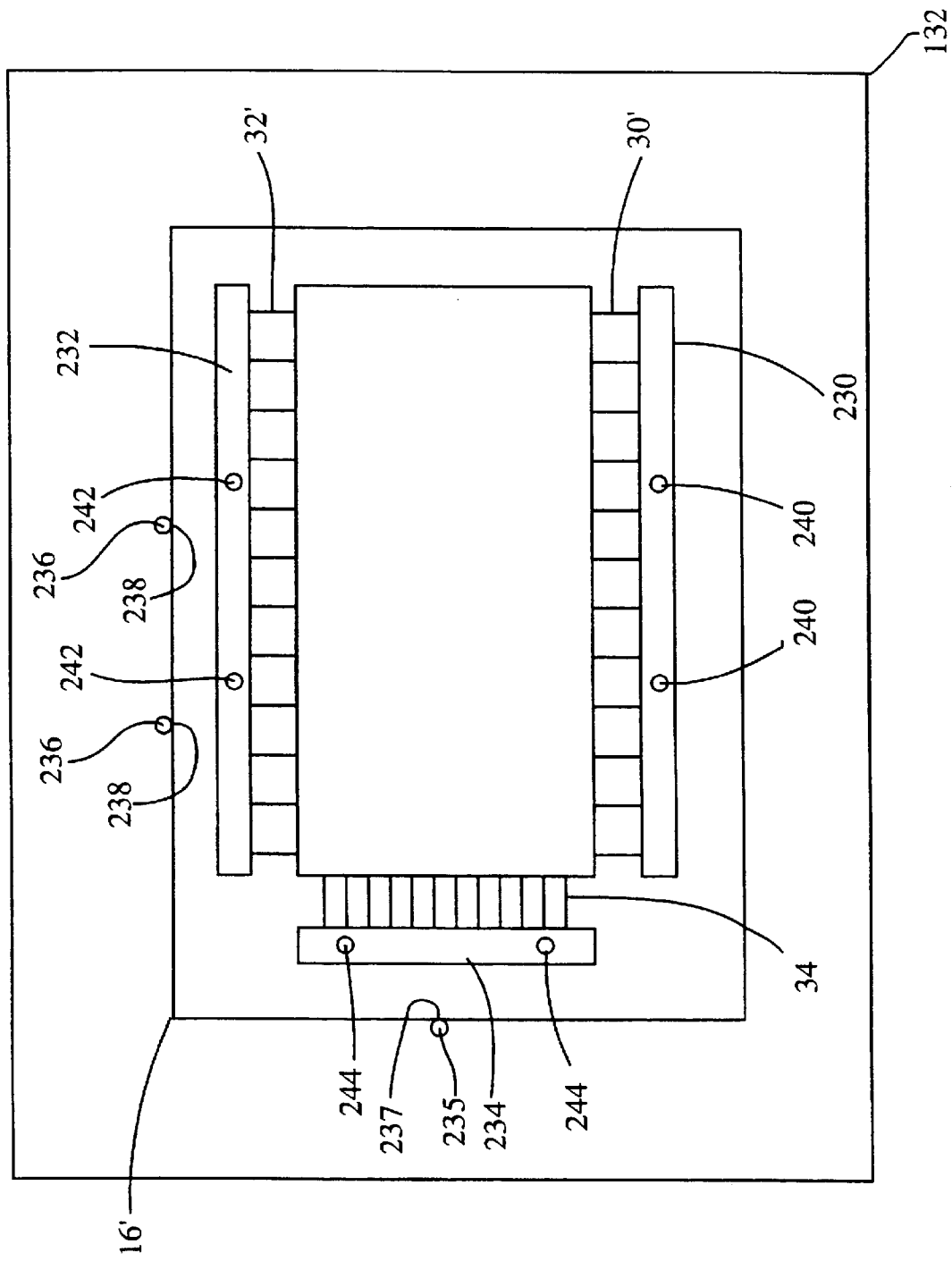
FIG. 6 is a diagrammatic representation of a top view of substrate aligned with a support of an embodiment of a substrate tester in accordance with the present invention.

FIG. 6 is a diagrammatic representation of a top view of an active matrix plate 16' aligned with the transparent support 132 after step 204. In FIG. 6, the active matrix plate 16' has gate electrodes 34' on only one side instead of two. Odd data electrodes 30' are shorted together by a shorting bar 230. Similarly, even data electrodes 32' are shorted together by a shorting bar 232. Likewise, the gate electrodes 34' are shorted together by a shorting bar 234. These electrodes are shorted together to minimize electrostatic discharge damage during handling in accordance with standard techniques.

Alignment posts 235 and 236 on the transparent support 132 are aligned with corresponding alignment sites 237 and 238 on the active matrix plate 16'. The posts 236 permit automated alignment by pushing the matrix plate 16' with lever arms and robots. Clearly, many arrangements of posts are possible. Alternatively, the posts 235 and 236 may merely be designated regions on the transparent support 132 requiring a different alignment scheme.

Point pair 240 on the shorting bar 230 indicates where a pair of probe leads would be placed under testing. A test voltage from the pattern generator 120 is sent to one of the pair, and the pattern generator 120 checks if the signal has been received. The precise position of the point pair 240 along the shorting bar 230 is unimportant. Similarly placed point pairs 242 on the shorting bar 232, and point pair 244 on the shorting bar 234 serve corresponding purposes.

Figure 7A:
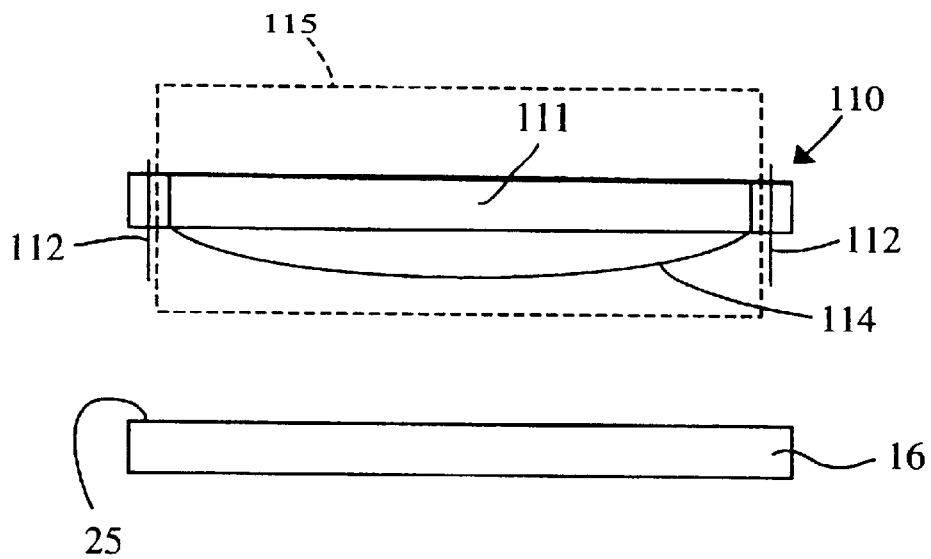
FIG. 7A is a diagrammatic representation of a side view of an embodiment of an integrated probe frame of the present invention before testing a substrate
Figure 7B:
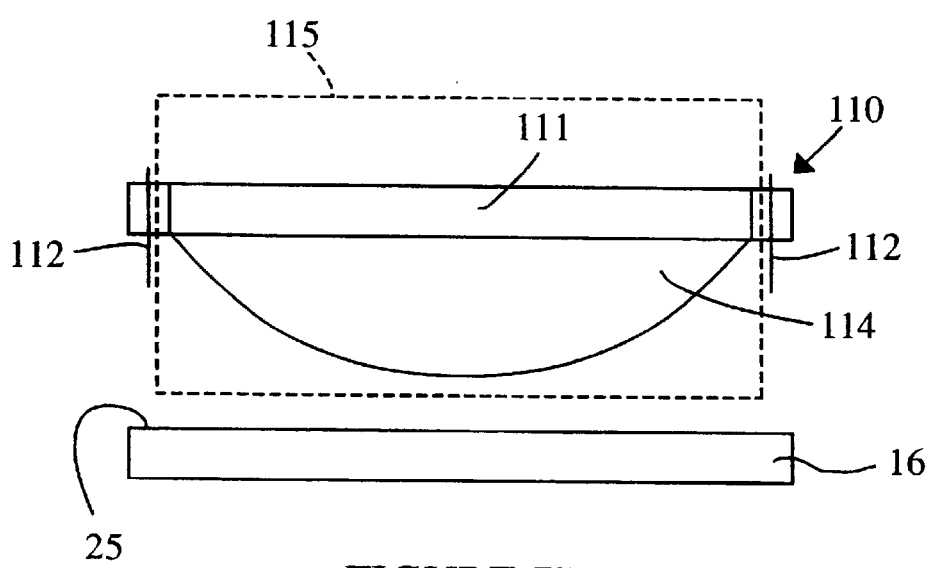
FIG. 7B is a diagrammatic representation of a side view of an embodiment of an integrated probe frame with inflated sensing material of the present invention before testing a substrate.
Figure 7C:
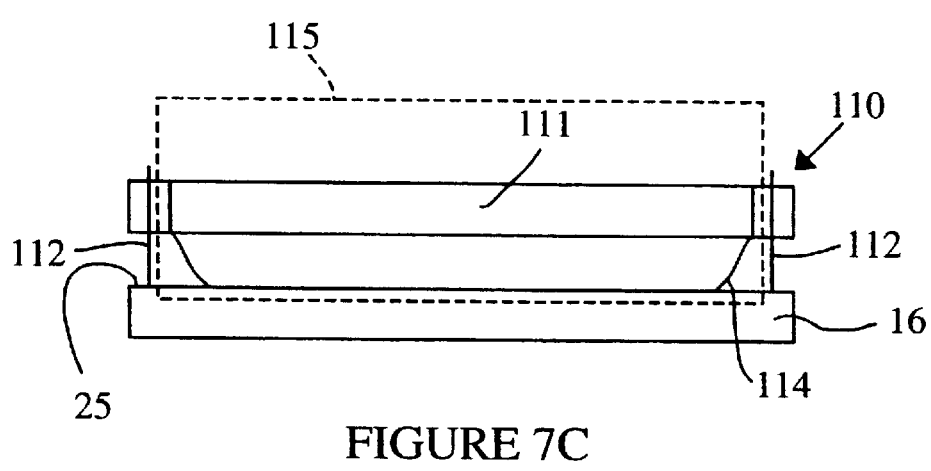
FIG. 7C is a diagrammatic representation of a side view of an embodiment of an integrated probe frame with inflated sensing material of the present invention in contact with a substrate during testing.

FIGS. 7A–7C diagrammatically illustrate steps 206, 208, and 210 described above with side views of the integrated probe frame 110 and active matrix plate 16. The deformable sensing head 115 is labeled with a dashed line and includes the sensing material 114. FIG. 7A shows the integrated probe frame 110 above the active matrix plate 16. The sensing material 114 is not inflated. FIG. 7B shows the sensing material 114 inflated as it would be after step 206. As shown, the inflated sensing material 114 has a convex shape whose lowest point contacts the surface 25 first. Thereafter, the mutual contact 250 increases outward as the deformable sensing head is lowered. FIG. 7C shows the results of steps 208 and 210. An area of mutual contact 250 is formed where the sensing material 114 meets the surface 25 of the active matrix plate 16.

Figure 8:
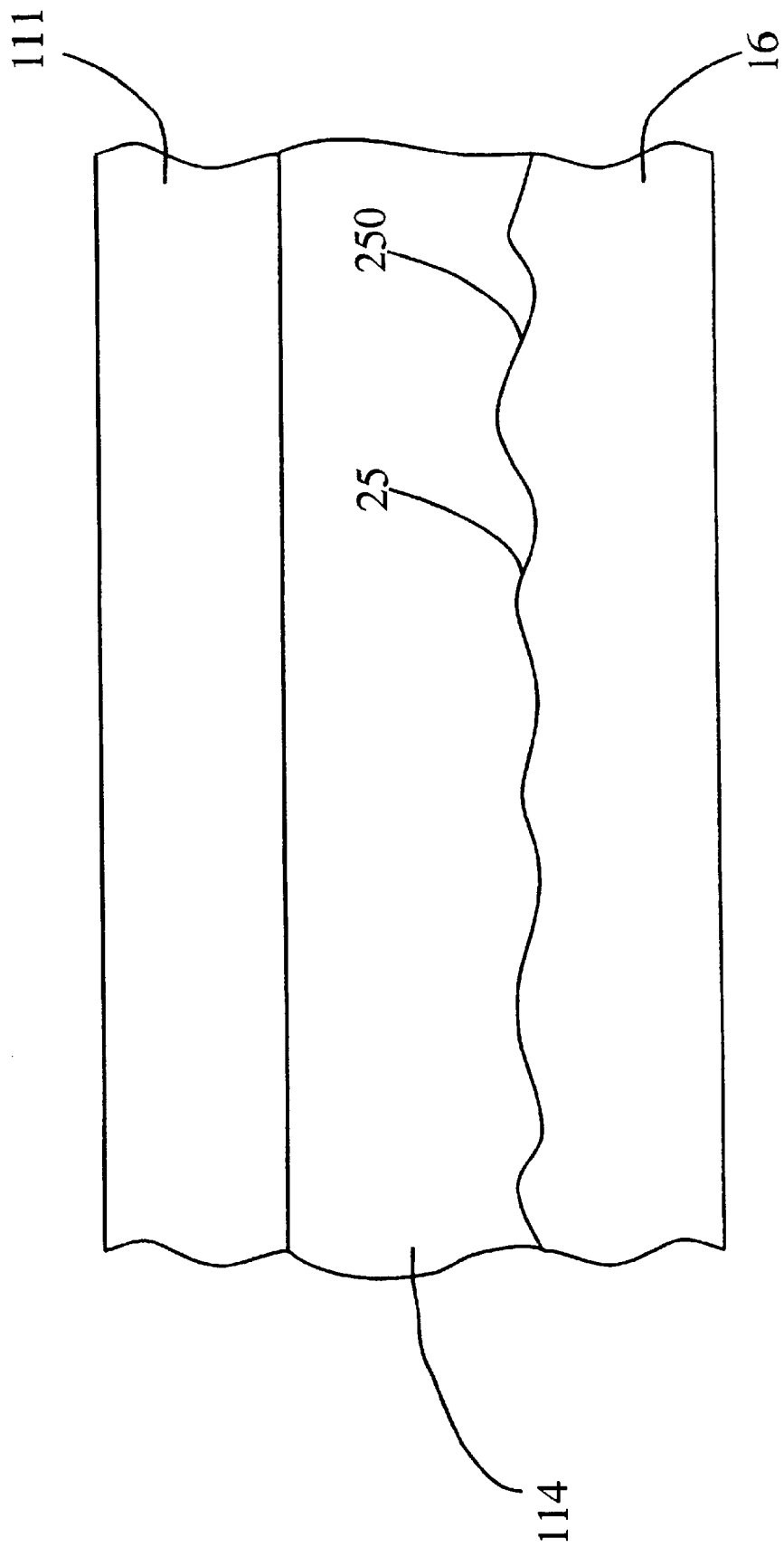
FIG. 8 is a diagrammatic representation of a side view of a mutual contact area between sensing material of the present invention and a substrate.

FIG. 8 diagrammatically illustrates a magnified side view of the mutual contact area 250. The portion of the surface of the sensing material 114 conforms with the surface 25 within the mutual contact area 250. Thus, the contact area is virtually absent of gaps inherent in the conventional use of rigid sensing material 47 as show in FIG. 2B. As previously mentioned, convex sensing material facilitates minimizing air bubbles between the sensing material 114 and the top surface 25.

Figure 9:
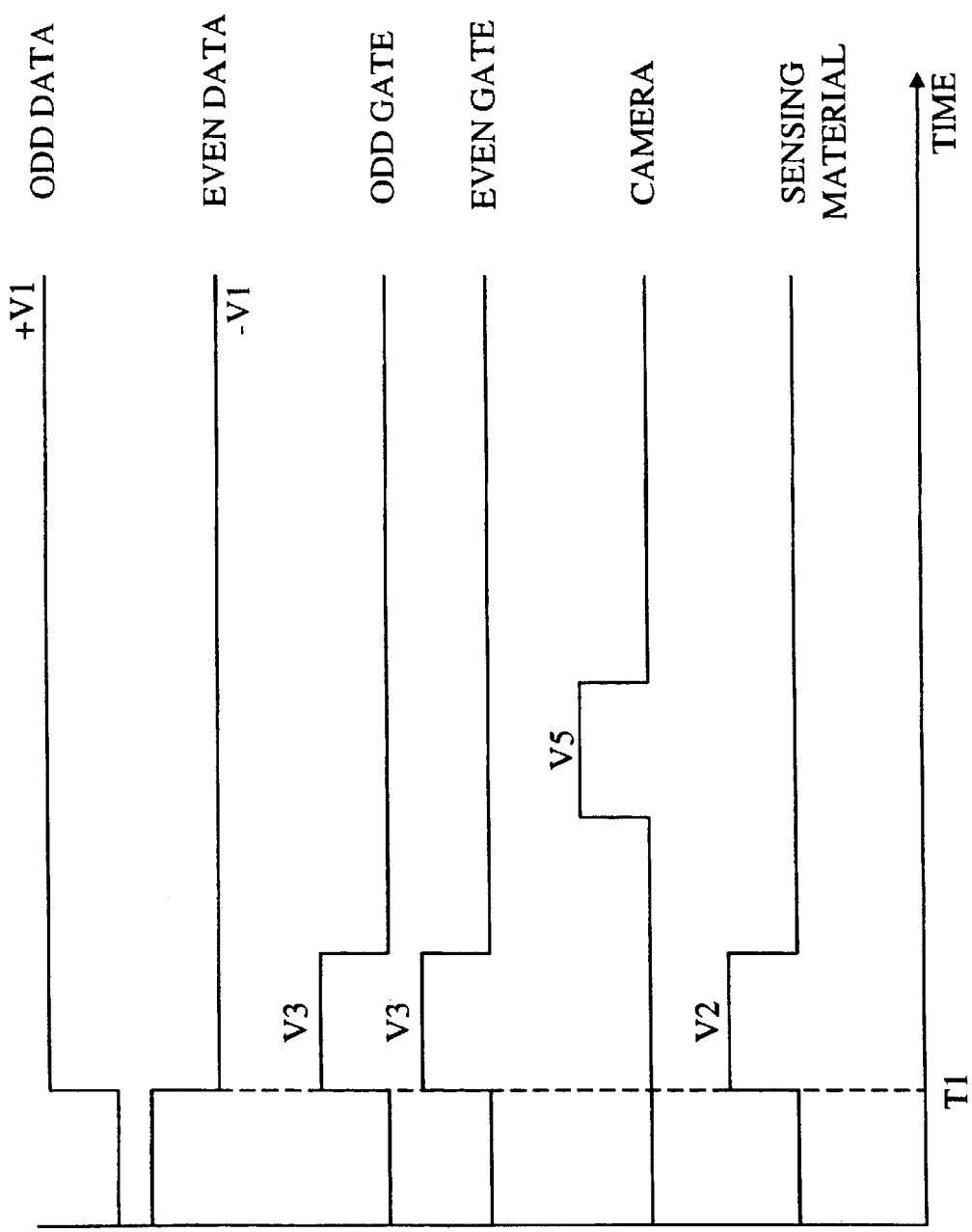
FIG. 9 is graph of signals generated by a pattern generator in accordance with the present invention.

FIG. 9 shows a sample set of signals transmitted by the pattern generator. Odd and even data signals of magnitude V1 are applied in step 212 to corresponding odd data electrodes 30 and even data electrodes 32 at time T1. As depicted, gate signals of magnitude V3 are simultaneously applied to odd gate electrodes 33 and even gate electrodes 34 to activate transistors 28 and pixel 14. A biasing signal of magnitude V2 is sent to the sensing material in step 214. After sending the test data signals and biasing the sensing material, the pattern generator switches the camera 150 on. In FIG. 9, a pulse turns the camera 150 on for a time interval and then turns it off.

Unlike previous test methods, only one application of test signals as shown in FIG. 9 to the active matrix plate 16 is required for testing. As mentioned in the description of a conventional method outlined in FIG. 4, four sets of test patterns are required for a given V1 under conventional testing.

While this invention has been described in terms of several preferred embodiments, it is contemplated that alterations, modifications and permutations thereof will become apparent to those skilled in the art upon a reading of the specification and study of the drawings. For example, a semiconductor chip, a wafer, integrated circuit, other type of liquid crystal display panel, or other electrically conductive substrate besides an active matrix plate may be tested. In addition, the substrate need not be flat. Furthermore, certain terminology has been used for the purposes of descriptive clarity, and not to limit the present invention. It is therefore intended that the following appended claims include all such alterations, modifications and permutations as fall within the true spirit and scope of the present invention.

What is claimed is:

1. A method of testing an electrically conductive substrate, the method comprising the steps of:

contacting a first portion of a surface of a sensing material to a first portion of a surface of the substrate to form a first contiguous area of intimate mutual contact area between the first portion of the surface of the sensing material and the first portion of the surface of the substrate and contacting a second additional portion of the surface of the sensing material to a second additional portion of the surface, thereby expanding the contiguous contact area to form a larger contiguous area of intimate mutual contact between the surface of the sensing material and the surface of the substrate;

applying a test signal to electrodes on the substrate and the sensing material;

illuminating the sensing material; and detecting light that has interacted with the sensing material to determine any changes induced in the sensing material as a result of defects in the substrate which show up upon the application of the test signal to the electrodes.

2. A method of testing as recited in claim 1 wherein the contacting step covers entirely the surface of the substrate with the sensing material.

3. A method of testing as recited in claim 1 wherein the sensing material is inflatable, the method further comprising inflating the sensing material such that a portion of the sensing material is in contact with the surface of the substrate while the sensing material is inflated.

4. A method of testing as recited in claim 1 further comprising a step of digitizing the light detected in the detecting step into electrical signals.

5. A method of testing as recited in claim 4 further comprising the step displaying the electrical signals on a video monitor.

6. A method of testing as recited in claim 1 wherein optical properties of the sensing material are heat sensitive whereby the detecting step determines heat changes on the substrate caused by said defects.

7. A method of testing as recited in claim 1 further comprising a step of aligning the substrate with respect to the sensing material.

* * * * *

UNITED STATES PATENT AND TRADEMARK OFFICE
CERTIFICATE OF CORRECTION

PATENT NO. : 6,285,207 B1
DATED : September 4, 2001
INVENTOR(S) : Andrew Listwan It is certified that error appears in the above-identified patent and that said Letters Patent is hereby corrected as shown below:

Column 1,
Line 24, delete "uphold" and insert -- hold --

Column 6,
Line 31, delete "particular" and insert -- particularly --
Line 53, insert -- is -- after "which"
Line 56, delete "?" and insert -- active --
Line 58, delete "1" after "material" and insert -- 114 --
Line 59, insert -- is heat -- after "114"

Column 7,
Line 19, delete "tab f" and insert -- tabulation of --
Line 43, insert -- 110 move down -- after "frame"

Column 8,
Line 8, delete "11" and insert -- 11 --
Line 10, delete "by" after "simply"
Line 22, delete "a" after "on"
Line 26, delete "2" and insert -- support 132 --

Column 12,
Line 2, insert -- of -- after "step"

Signed and Sealed this

Sixteenth Day of July, 2002

Attest:

JAMES E. ROGAN
Attesting Officer
Director of the United States Patent and Trademark Office